US012728074B2

(12) United States Patent
Chalah

(10) Patent No.: US 12,728,074 B2
(45) Date of Patent: Sep. 8, 2026

(54) ENHANCED INSPECTION OF MEDICAMENTS AFTER LOADING OF BLISTER CARD PRESCRIPTIONS

(71) Applicant: Synergy Medical BRG Inc., Longueuil (CA)

(72) Inventor: Abderrahmane Chalah, L'Île-Bizard (CA)

(73) Assignee: SYNERGY MEDICAL BRG INC., Longueuil (CA)

( * ) Notice: Subject to any disclaimer, the term of this patent is extended or adjusted under 35 U.S.C. 154(b) by 267 days.

(21) Appl. No.: 18/619,429

(22) Filed: Mar. 28, 2024

(65) Prior Publication Data

US 2024/0358591 A1 Oct. 31, 2024

Related U.S. Application Data

(60) Provisional application No. 63/584,622, filed on Sep. 22, 2023, provisional application No. 63/498,100, filed on Apr. 25, 2023.

(51) Int. Cl.

*A61J 1/00* (2023.01)
*A61J 1/03* (2023.01)

(Continued)

(52) U.S. Cl.

CPC ............ *A61J 1/035* (2013.01); *G06T 1/0007* (2013.01); *G16H 20/13* (2018.01)

(58) Field of Classification Search

CPC .. A61J 1/035; A61J 7/04; A61J 7/0069; A61J 7/0445; A61J 7/0481; A61J 1/10;

(Continued)

(56) References Cited

U.S. PATENT DOCUMENTS 4,573,606 A * 3/1986 Lewis .................. A61J 7/0481 221/3
4,763,810 A * 8/1988 Christiansen ......... A61J 7/0481 221/3

(Continued)

FOREIGN PATENT DOCUMENTS

CA 2702073 C 12/2014
CA 2966186 A1 5/2016

(Continued)

OTHER PUBLICATIONS

International Preliminary Report on Patentability issued in PCT/CA2024/050452; Mailed: Nov. 6, 2025, (5 pp).

(Continued)

*Primary Examiner* — Jacob A Smith
(74) *Attorney, Agent, or Firm* — Myers Bigel, P.A.

(57) ABSTRACT

A method for inspecting medicaments loaded into wells of a blister card includes the steps of:

inserting a blister card loaded with medicaments in a plurality of wells into an inspection holder in a housing;
inverting the blister card so that the medicaments descend through chutes of a funnel of the inspection holder, each of the chutes corresponding to a well of the blister card, wherein descension of the medicaments is stopped by a cover that overlies the chutes;
capturing images of the medicaments through the cover; and
determining, based on the captured images, whether the medicaments in the blister card were correctly loaded.

13 Claims, 17 Drawing Sheets

(51) Int. Cl.
*G06T 1/00* (2006.01)
*G16H 20/13* (2018.01)

(58) Field of Classification Search
CPC .. A61J 2200/30; A61J 2205/10; G16H 20/13; G06T 1/007; B65B 9/00; B65B 9/08; B65B 65/08
USPC .......................................... 53/473, 111
See application file for complete search history.

(56) References Cited

U.S. PATENT DOCUMENTS 7,110,602 B2 9/2006 Krause
7,894,656 B2 2/2011 Kim
7,946,101 B1 5/2011 Mcgonagle et al.
8,019,471 B2 * 9/2011 Bogash .................. G07F 9/026 700/242
8,230,662 B2 7/2012 Boutin
8,682,047 B2 3/2014 Lang et al.
8,727,208 B2 5/2014 Poisner
8,861,816 B2 10/2014 Lang et al.
8,914,146 B2 12/2014 Carson et al.
8,943,779 B2 2/2015 Amano et al.
8,966,863 B2 3/2015 Amano et al.
9,084,714 B2 7/2015 Okuma
9,098,900 B2 8/2015 Helgason et al.
9,111,357 B2 8/2015 Brossette et al.
9,116,887 B2 8/2015 Botten
9,177,223 B2 11/2015 Mudge
9,238,518 B2 1/2016 Luciano et al.
9,311,451 B2 4/2016 Bae et al.
9,313,464 B2 4/2016 Pellerin et al.
9,334,096 B2 5/2016 Luciano et al.
9,387,155 B2 7/2016 Morioka et al.
9,406,127 B2 8/2016 Helgason et al.
9,412,176 B2 8/2016 Song et al.
9,466,004 B2 10/2016 Zheng et al.
9,672,420 B2 6/2017 Apell et al.
9,776,755 B2 10/2017 Kondo et al.
9,779,216 B2 10/2017 Siegel et al.
9,842,257 B2 12/2017 Gershtein et al.
9,858,497 B2 1/2018 Song et al.
9,922,419 B2 3/2018 Takahashi
9,994,347 B2 6/2018 Yuyama et al.
10,007,993 B2 6/2018 Takahashi
10,229,321 B2 3/2019 Gershtein et al.
10,262,114 B2 4/2019 Braun
10,314,767 B2 6/2019 Hasegawa
10,317,348 B2 6/2019 Van Den Brink
10,351,285 B2 7/2019 Sweet et al.
10,402,960 B2 9/2019 Ebata
10,410,337 B2 9/2019 Franchi
10,435,192 B2 10/2019 Luciano et al.
10,438,336 B2 10/2019 Takamori
10,467,477 B2 11/2019 Gershtein et al.
10,565,545 B2 2/2020 Yonaha et al.
10,713,540 B2 7/2020 Zhang et al.
10,719,731 B2 7/2020 Song et al.
10,741,275 B2 8/2020 Patel
10,762,614 B2 9/2020 Yuyama et al.
10,831,865 B2 11/2020 Van De Craen
10,869,813 B1 * 12/2020 Mazur ..................... B32B 27/08
10,872,688 B2 12/2020 Swarvar et al.
10,892,048 B2 1/2021 Reddy et al.
10,896,764 B2 1/2021 Yonaha et al.
10,937,152 B2 3/2021 Segawa
10,940,093 B2 3/2021 Williamson et al.
11,039,091 B2 6/2021 Holmes et al.
11,065,180 B2 7/2021 Grosfils et al.
11,156,560 B2 10/2021 Inoguchi
11,189,372 B2 11/2021 Poirier et al.
11,195,042 B2 12/2021 Iwami
11,237,115 B2 2/2022 Inoguchi
11,341,357 B2 5/2022 Iwami
11,357,703 B2 6/2022 Zoczek et al.
11,379,979 B2 7/2022 Markson et al.
11,404,153 B2 8/2022 Yokouchi
11,419,792 B2 8/2022 Jochemsen et al.
11,501,866 B2 11/2022 Iwami et al.
11,595,595 B2 2/2023 Holmes et al.
11,605,261 B2 3/2023 Boutin
11,776,674 B2 10/2023 Poirier et al.
2012/0096807 A1 * 4/2012 Okuma ..................... A61J 1/10 53/111 R
2016/0104277 A1 4/2016 Takamori
2018/0177682 A1 6/2018 Tanaka
2019/0088070 A1 * 3/2019 Patel ...................... G16H 20/13
2019/0178815 A1 6/2019 Tojo
2019/0269576 A1 9/2019 Grosfils et al.
2020/0058385 A1 2/2020 Yokouchi
2020/0265938 A1 8/2020 Low
2020/0402632 A1 12/2020 Van Schelven et al.
2021/0019886 A1 1/2021 Iwami
2021/0070548 A1 3/2021 Hawkes et al.
2021/0082584 A1 3/2021 Yonaha et al.
2021/0090704 A1 3/2021 Poirier et al.
2021/0161767 A1 6/2021 Holmes
2022/0156908 A1 5/2022 Van Schelven
2022/0254172 A1 8/2022 Bugay et al.
2022/0261982 A1 8/2022 Bugay et al.
2022/0392600 A1 12/2022 Okutsu et al.
2023/0043100 A1 2/2023 Davis et al.
2023/0098966 A1 3/2023 Lewis et al.
2023/0101967 A1 3/2023 Holmes
2023/0121169 A1 4/2023 Bouthiette
2023/0391482 A1 12/2023 Hébert et al.

FOREIGN PATENT DOCUMENTS

CA 2966225 A1 5/2016
CN 105307622 B 3/2019
CN 106104260 B 7/2019
CN 105073082 B 9/2019
CN 104582670 B 11/2019
CN 111095262 A 5/2020
CN 110418627 B 11/2021
CN 113811761 A 12/2021
EP 2025601 B1 9/2011
EP 3315112 A1 5/2018
EP 3593353 A1 1/2020
EP 3675032 A1 7/2020
EP 4024400 A1 7/2022
JP 6599934 B2 10/2019
JP 6797549 B2 11/2020
JP 7125510 B2 8/2022
JP 7244636 B2 3/2023
KR 100787807 B1 12/2007
WO 2019170685 A1 9/2019
WO 2022065275 A1 3/2022
WO 2022081874 A1 4/2022
WO 2022211423 A1 10/2022
WO 2023032635 A1 3/2023
WO 2024058662 A1 3/2024

OTHER PUBLICATIONS

International Search Report and Written Opinion corresponding to PCT/CA2024/050452, Mailed: Jun. 20, 2024, (8 pages).

* cited by examiner

ENHANCED INSPECTION OF MEDICAMENTS AFTER LOADING OF BLISTER CARD PRESCRIPTIONS

RELATED APPLICATION

The present application claims priority from and the benefit of U.S. Provisional Application Nos. 63/498,100, filed Apr. 25, 2023, and 63/584,622, filed Sep. 22, 2023, the disclosures of which are hereby incorporated herein by reference in full.

FIELD OF THE INVENTION

The present invention is directed to the inspection of medicaments loaded into blister cards.

BACKGROUND OF THE INVENTION

Doses of medication over prescribed periods vary as a function of the type of medication and the condition of the patient. Patients are often required to take a plurality of doses over different periods of a day, and this can lead to confusion. It may be difficult for a patient to respect the prescription details (e.g., intake time, quantity) when the doses and the types of medication are numerous.

One well known method used by pharmacists to overcome this problem is to provide the patient with a dose pack having an array of receptacles, with each receptacle corresponding to a particular time of a day at which medication is to be taken. Such packs typically contain four receptacles per day for seven days, and these receptacles are in the form of sealed cups or wells filled by pharmacists with appropriate medication as determined by physicians' prescription. Some types of these dose packs are known as "blister packs" or "blister cards," which typically include a plurality of wells or pockets arranged in a grid of rows and columns; for many blister cards, the wells in a row may represent the medications taken at different times on a particular day, with each row representing a different day. Exemplary blister cards may have seven rows, each row including four wells for four different administration times during that day, such that the card represents a week's worth of medications for the patient. Alternative arrangements include 4×8 and 5×7 cards. Another alternative is a 28 or 31 day card, wherein a set of three or four such cards may represent a month's worth of medications, with each card providing medications for a particular time of day (e.g., one "breakfast" card, one "lunch" card, etc.). Also, some blister cards may be oriented 90 degrees from this arrangement, such that the columns represent different days.

The process of preparing these dose packs by hand can be labor-intensive, in that each receptacle must be filled individually and may contain different medications compared to other receptacles in the same pack. Therefore, although the dose pack facilitates the intake of medication by patients, a substantial amount of time is required to fill these packs by pharmacists or pharmacy staff.

As a result, automated systems for filling dose packs have been developed. For example, U.S. Pat. No. 8,230,662 to Boutin (the disclosure of which is hereby incorporated herein by reference in full) describes a system for filling medication dose packs with oral-solid medication items. The system (sold under the name SynMed™ XF by Synergie Medicale, (Quebec, Canada) comprises storage tray drawers, each of which has multiple storage trays or canisters. Each storage tray stores a specific type of oral solid medication item. The storage tray drawers are displaceable to a drawn position to expose the storage trays thereof. A table supports blister cards having a plurality of receptacles arranged in rows, with each receptacle typically associated with an intake day and time of a patient prescription file. A dispensing mechanism, provided with an output arm, is displaceable along the axes X, Y and Z in order to transport medication items from the medication storage trays to the wells of the blister cards. The dispensing mechanism includes individual pipettes that, via suction, lift individual pills from storage trays and deposit them into dose packs residing on the table. Another variation of the system is shown in U.S. Pat. No. 11,605,261 to Boutin, the disclosure of which is also incorporated by reference herein in full, a version of which is sold under the name SynMed™ Ultra.

Although such medication loading systems tend to be very accurate, in many jurisdictions pharmaceutical regulations require that the contents of the wells of the blister cards be inspected to ensure that the correct medication and dosage is in each well of the blister cards according to the patient's prescriptions. This inspection is typically carried out by a pharmacist, who will visually inspect the medications in each well prior to a sealing cover or sheet being applied to the blister card to maintain the medications in the wells. There have been attempts to provide automated inspection systems to save the pharmacist the time of performing this inspection. Such systems typically use a camera that takes one or more images of each well of a blister card prior to the application of the sealing sheet. However, when multiple medicaments are present in a single well, in some instances one of the pills may obscure one or more of the other pills, thereby making visual inspection with the camera difficult, if not impossible, and often requiring the pharmacist to remove pills from the well in order to clearly view all cell contents.

In view of the foregoing, it may be desirable to provide systems and methods for enhanced inspection of medicaments loaded into blister cards.

SUMMARY

As a first aspect, embodiments of the invention are directed to a system for inspecting medicaments of a pharmaceutical prescription contained in a blister card, the blister card having a plurality of wells, each of the wells including one or more medicaments. The system comprises a housing and an inspection holder rotatably mounted in the housing. The inspection holder comprises: a funnel including a plurality of chutes with first and second ends, each of the first ends of the chutes in communication with a respective through hole, wherein each of the second ends has a larger area that is larger than a surface area of the corresponding first end; a cover mounted to the funnel to cover the second ends of the chutes; a structure for mounting a blister card filled with medicaments adjacent the first ends of the chutes; a drive unit operatively connected with the inspection holder and configured to rotate the inspection holder between a first position, in which the cover is above the funnel, and an inverted second position, in which the cover is below the funnel; and a camera positioned below the inspection holder and configured to capture images of medicaments in the second ends of the chutes when the inspection holder is in the second position, the camera operatively connected with an inspection unit that is configured to determine whether medicaments in the captured images match medicaments expected to be in the captured images.

As a second aspect, embodiments of the invention are directed to a method for inspecting medicaments loaded into wells of a blister card. The method comprises the steps of:

(a) inserting a blister card loaded with medicaments in a plurality of wells into an inspection holder in a housing;
(b) inverting the blister card so that the medicaments descend through chutes of a funnel of the inspection holder, each of the chutes corresponding to a well of the blister card, wherein descension of the medicaments is stopped by a cover that overlies the chutes;
(c) capturing images of the medicaments through the cover; and
(d) determining, based on the captured images, whether the medicaments in the blister card were correctly loaded.

DETAILED DESCRIPTION OF THE INVENTION

Figure 1:
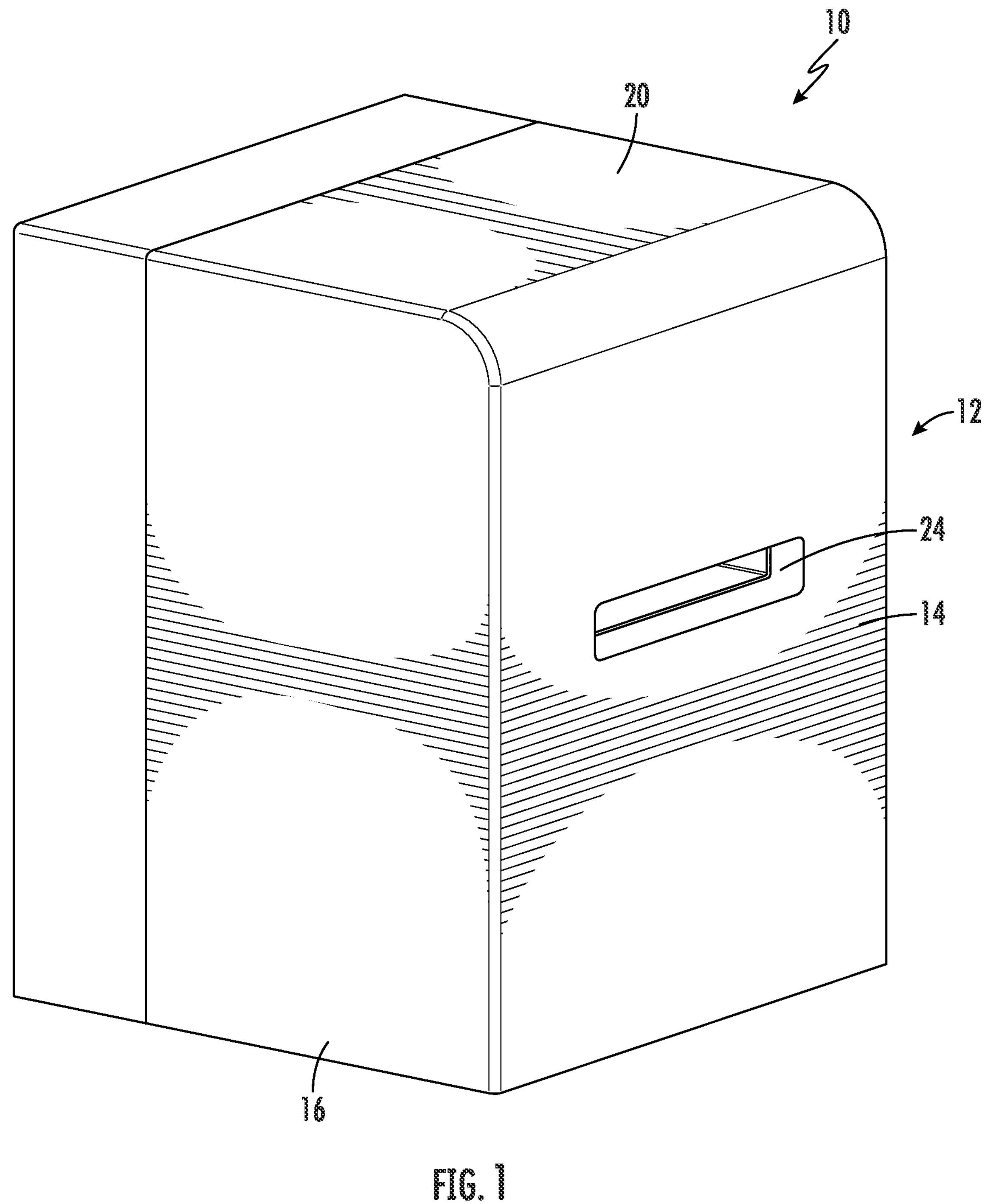
FIG. 1 is a front perspective view of a blister card inspection system according to embodiments of the invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the expression "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

Figure 2:
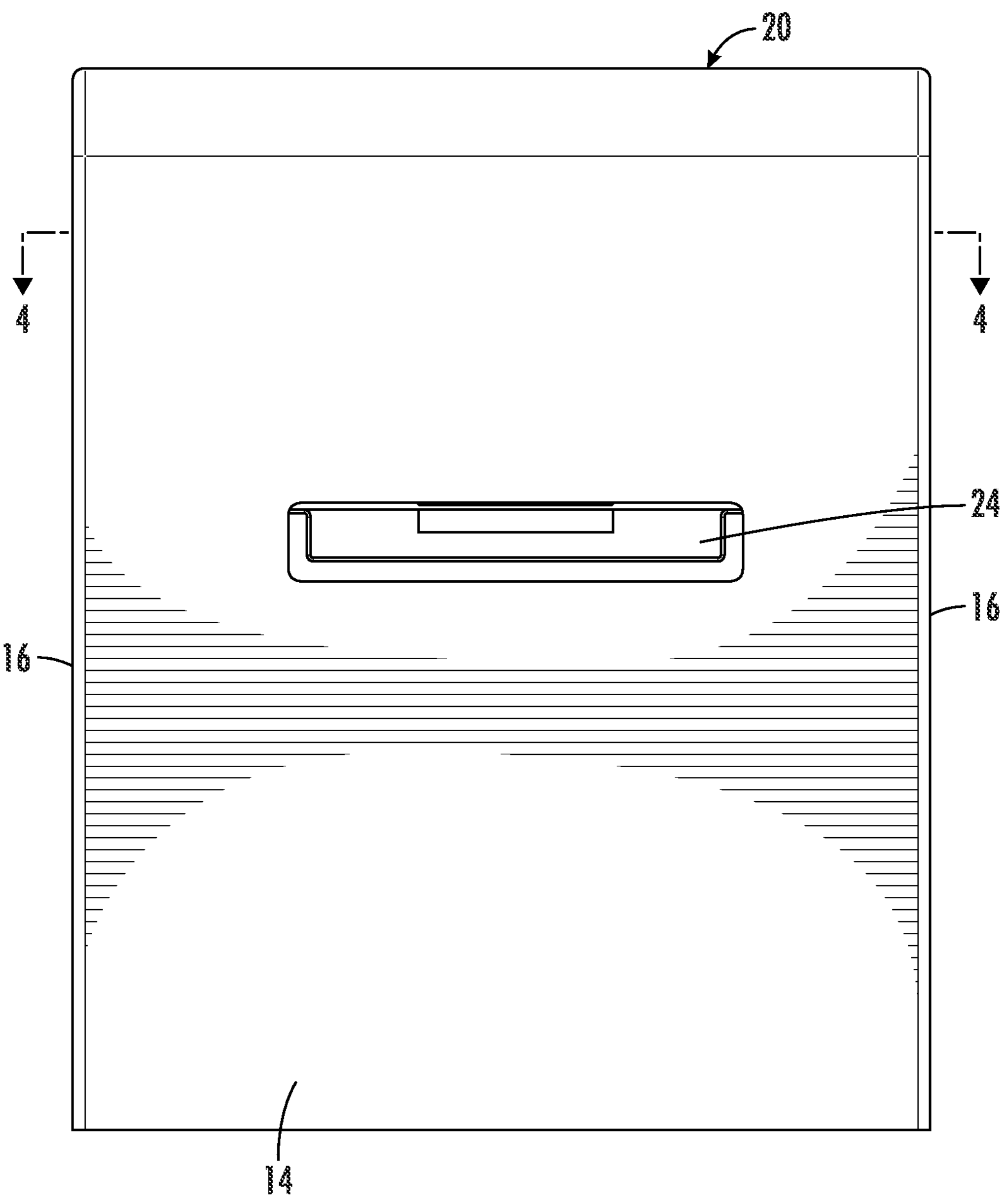
FIG. 2 is a front view of the system of FIG. 1.
Figure 3:
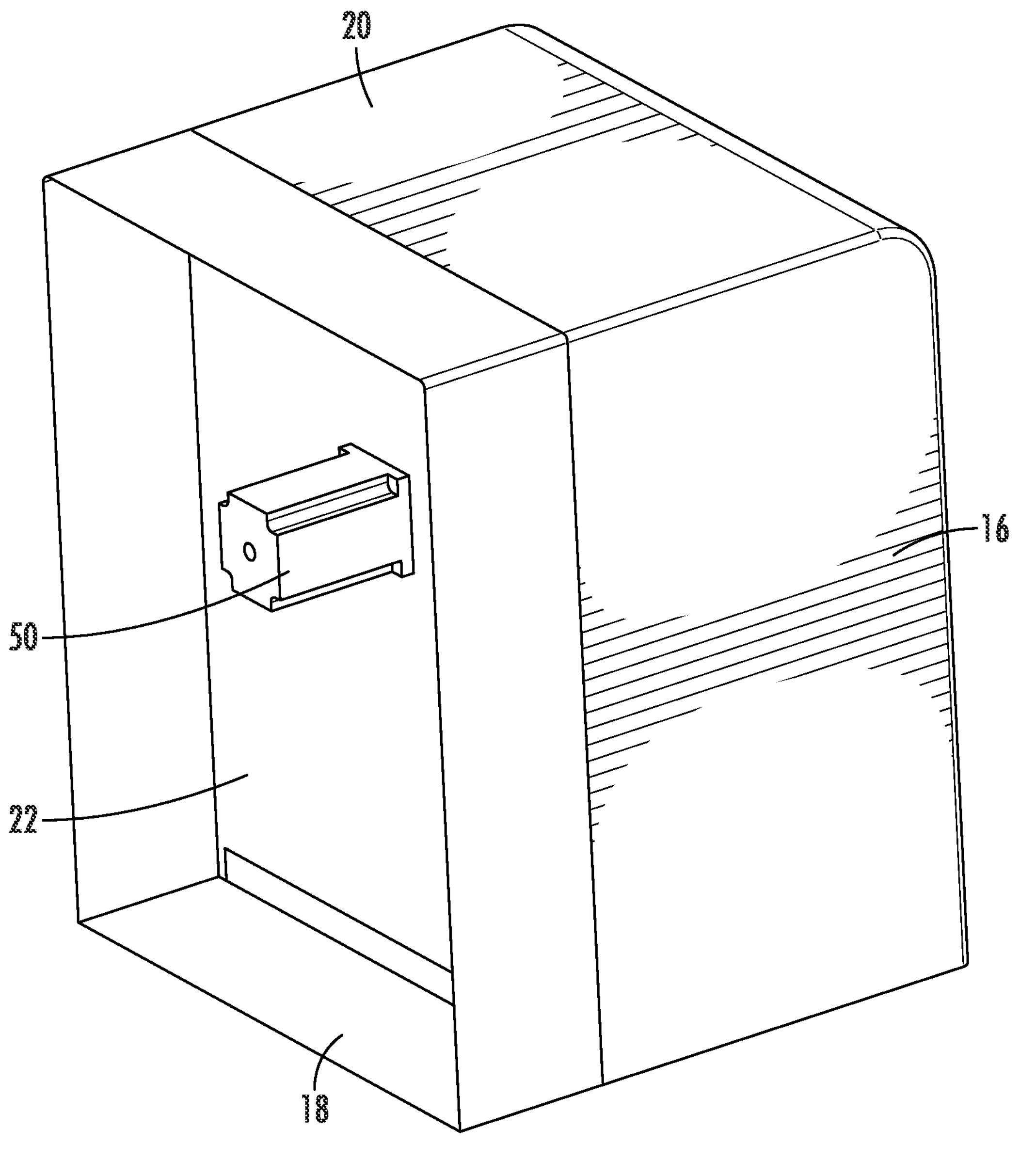
FIG. 3 is a rear perspective view of the system of FIG. 1.
Figure 4:
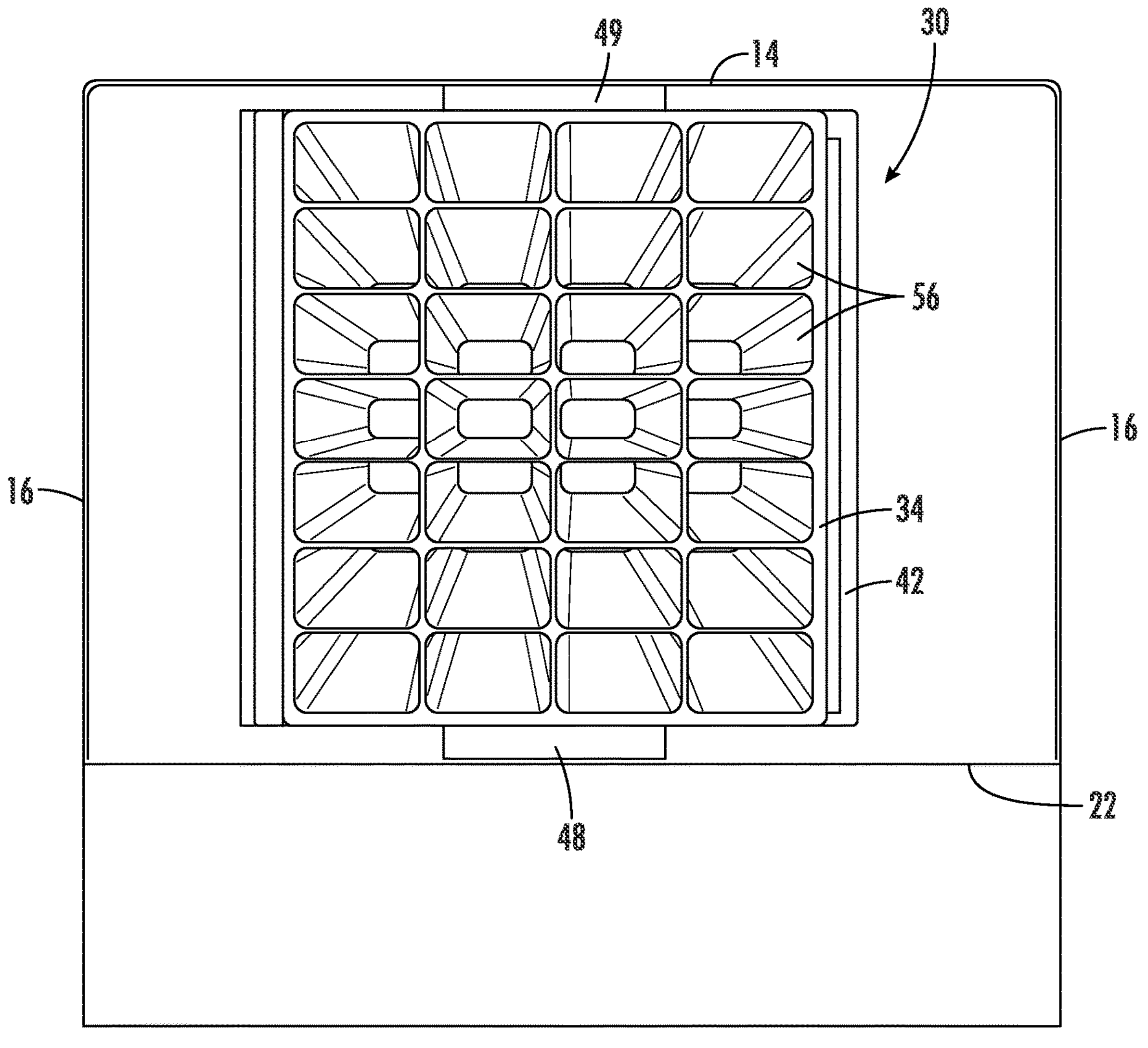
FIG. 4 is top section view of the system of FIG. 1 taken along lines 4-4 of FIG. 2.
Figure 5:
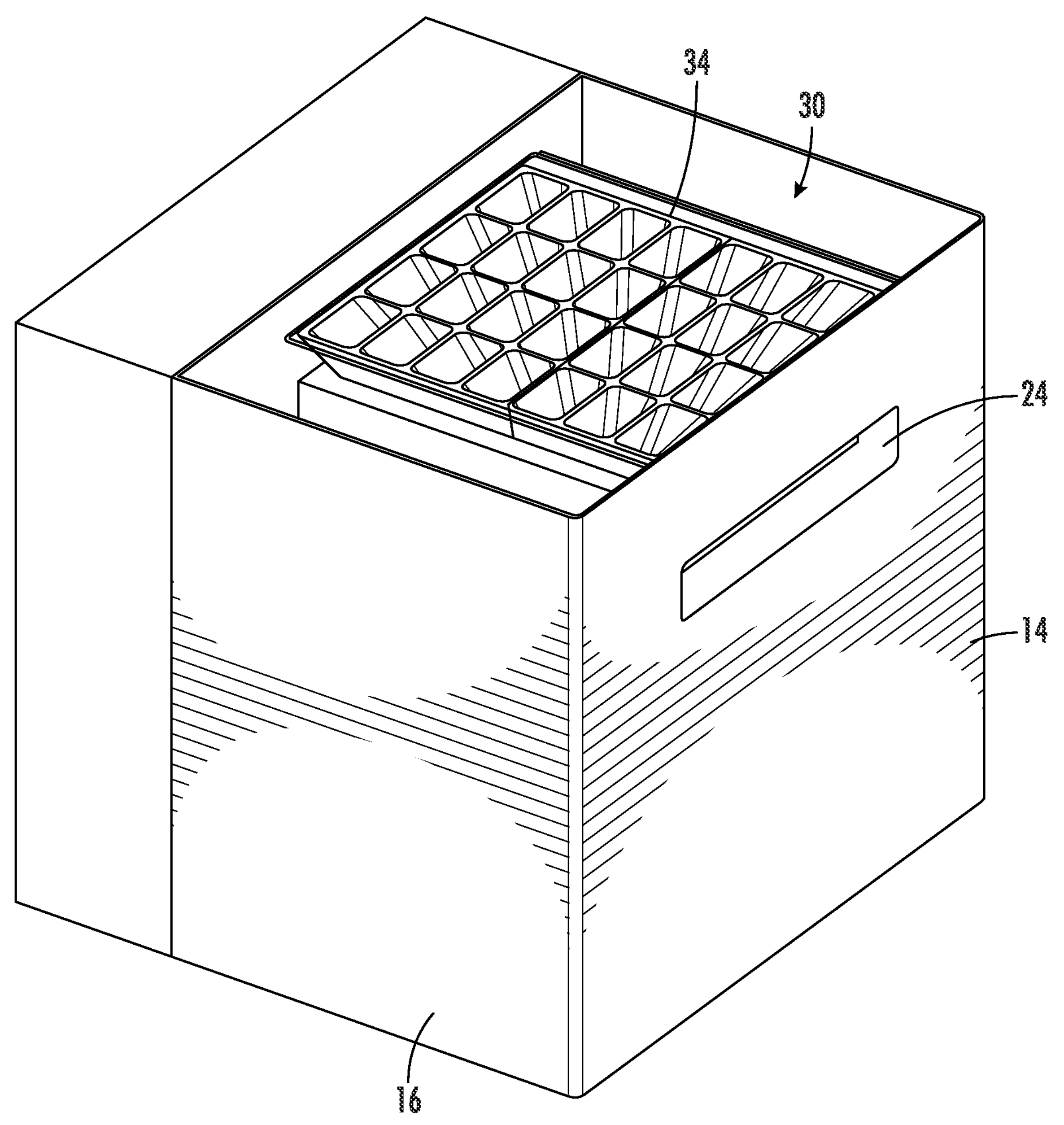
FIG. 5 is a top perspective section view of the system of FIG. 1 taken along lines 4-4 of FIG. 2.

Referring now to the figures, a system for inspecting medicaments loaded into a blister card is shown in FIGS. 1-11B and is designated broadly at 10. Referring first to FIGS. 1-3, the system 10 includes a generally box-shaped housing 12 with a front wall 14, side walls 16, a floor 18, a ceiling 20, and a rear wall 22. As can be seen in FIG. 3, the rear wall 22 is inserted slightly from the rear edges of the side walls 16, floor 18 and ceiling 20. The front wall 14 includes a horizontal slot 24 that provides access to a blister card inspection holder 30 (see, e.g., FIGS. 6-11B), described in greater detail below.

Figure 6:
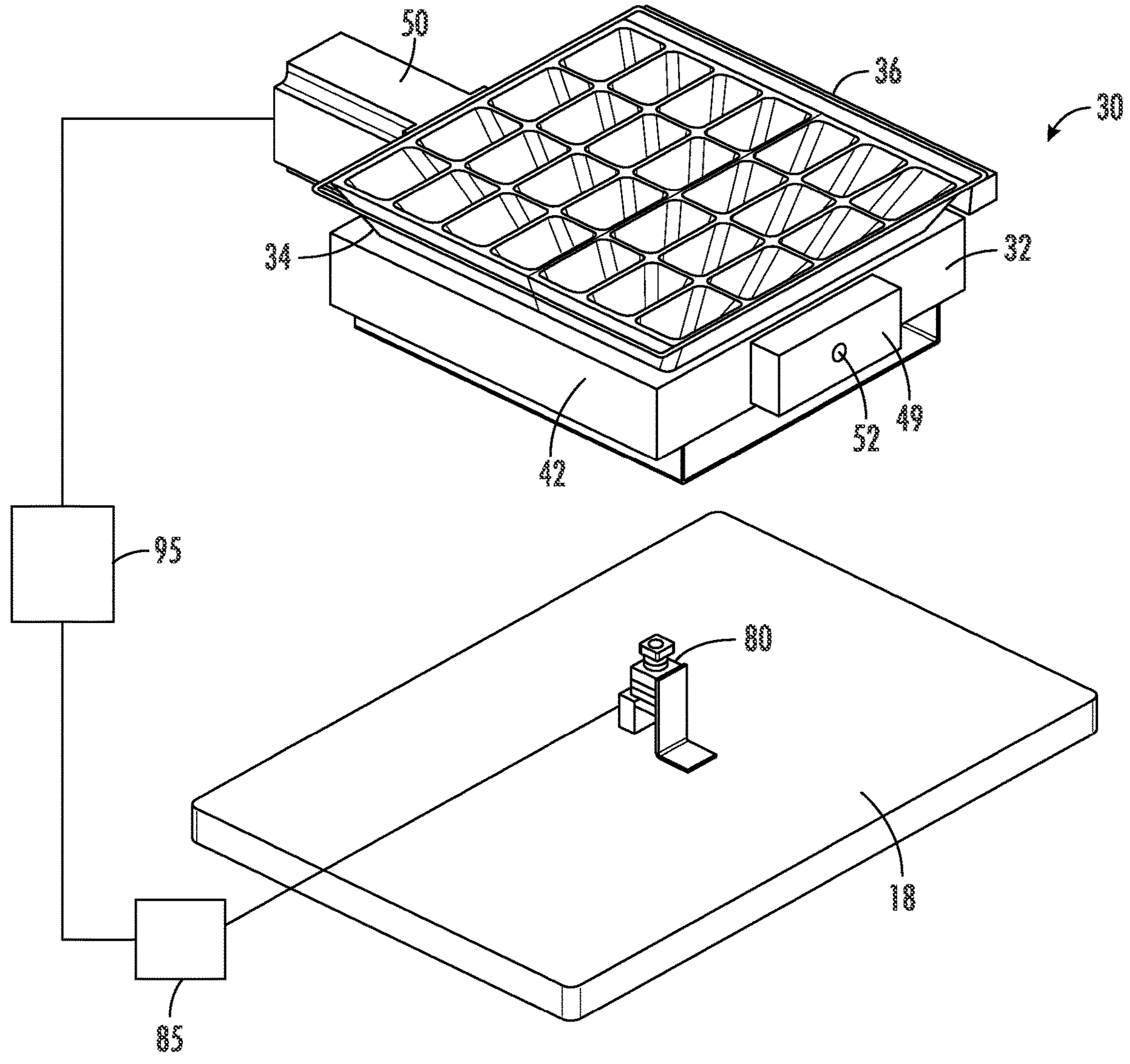
FIG. 6 is a front perspective view of the inspection holder and camera of the system of FIG. 1.
Figure 7:
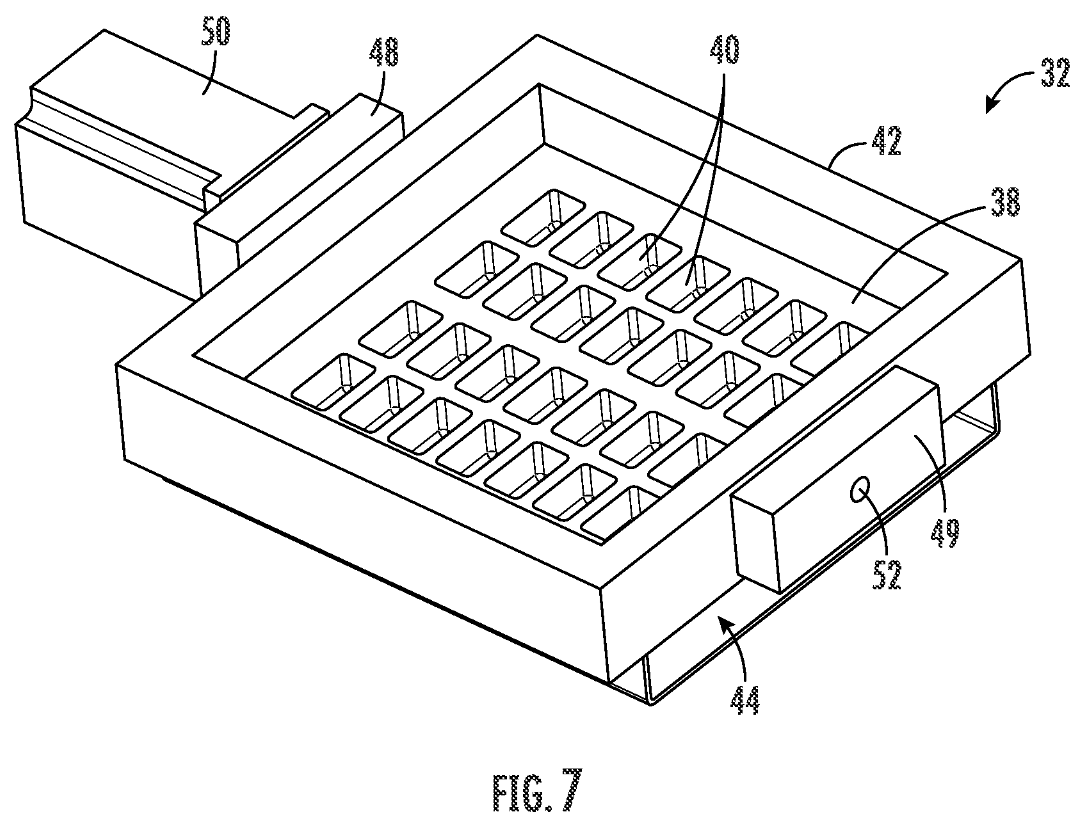
FIG. 7 is a front perspective view of the base of the inspection holder of FIG. 6.
Figure 8:
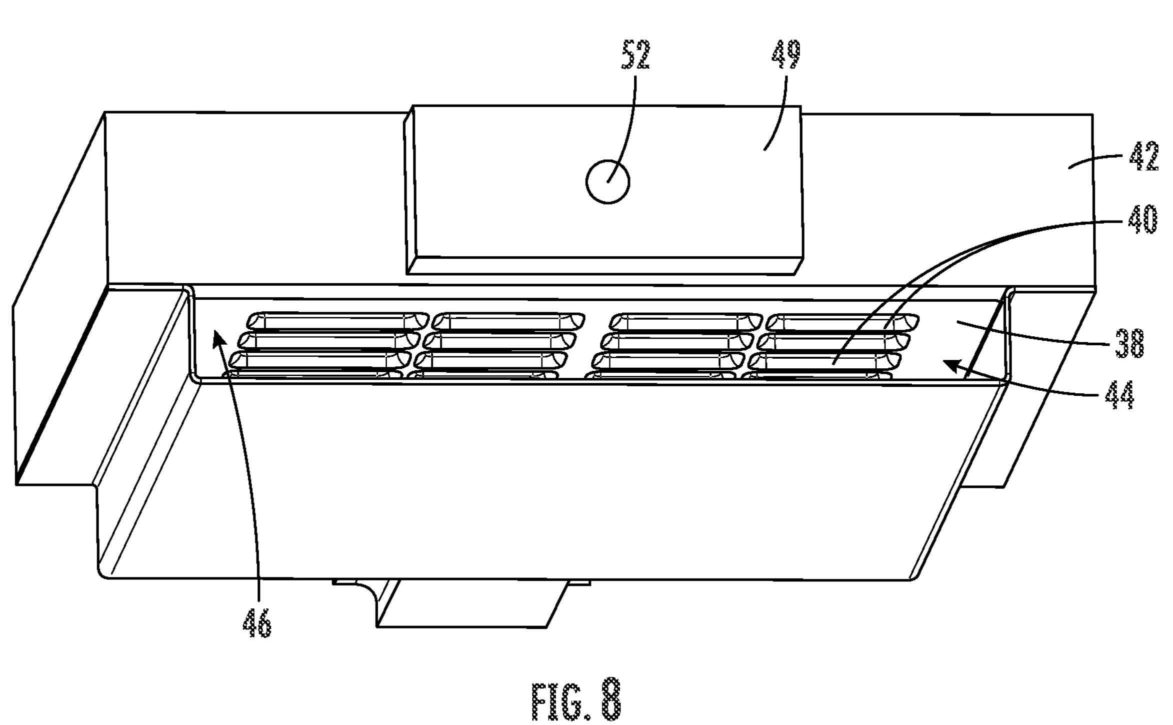
FIG. 8 is a front, bottom perspective view of the base of FIG. 7.

Referring first to FIG. 6, the blister card inspection holder 30 includes a base 32, a multi-chute funnel 34, and a transparent cover 36. As can be seen in FIGS. 7 and 8, the base 32 is generally square, with a floor 38 having a grid of oblong through holes 40. The base 32 also has a peripheral rim 42. A receiving pocket 44 depends from the floor 38 beneath the holes 40 and includes a front opening 46. A motor 50 (see FIG. 3) or other drive unit is mounted to the rear surface of the rear wall 22 of the housing 12. A shaft 52 is attached to the motor 50 and extends through a bearing block 48 mounted to the forward surface of the rear wall 22, the floor 38, and a bearing block 49 mounted to the rear surface of the front wall 14 of the housing 12 (see FIGS. 4, 7 and 8). The shaft 52 is free to rotate relative to the bearing blocks 48, 49, but is fixed relative to the base 32. As such, rotation of the shaft 52 by the motor 50 enables the base 32 (and in turn any components attached thereto) to rotate about the axis defined by the shaft 52.

Figure 9:
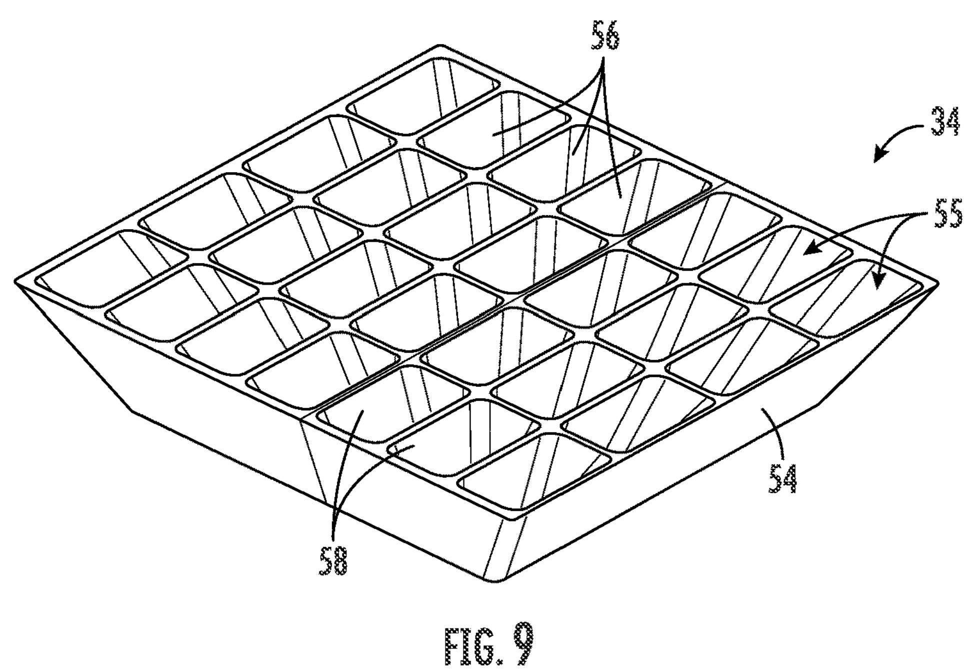
FIG. 9 is a front perspective view of the funnel of the inspection holder of FIG. 6.
Figure 10:
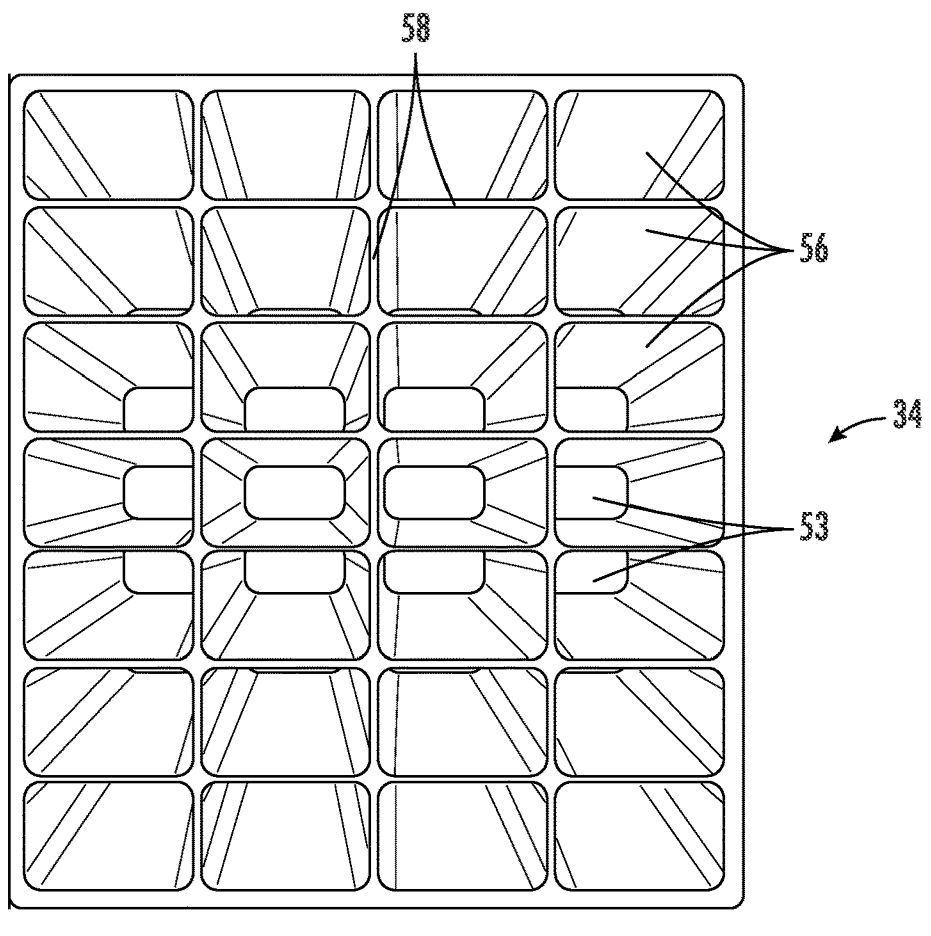
FIG. 10 is a top view of the funnel of FIG. 9.
Figure 11A:
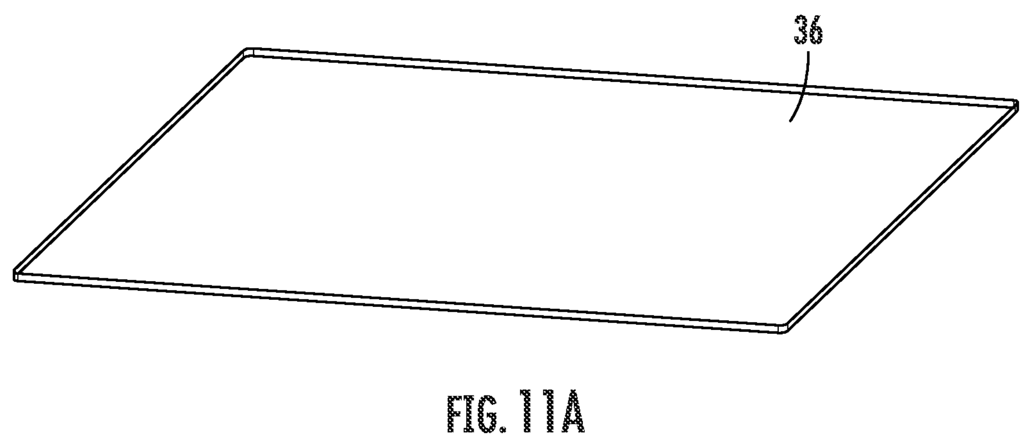
FIG. 11A is a perspective view of the cover of the inspection holder of FIG. 6.
Figure 11B:
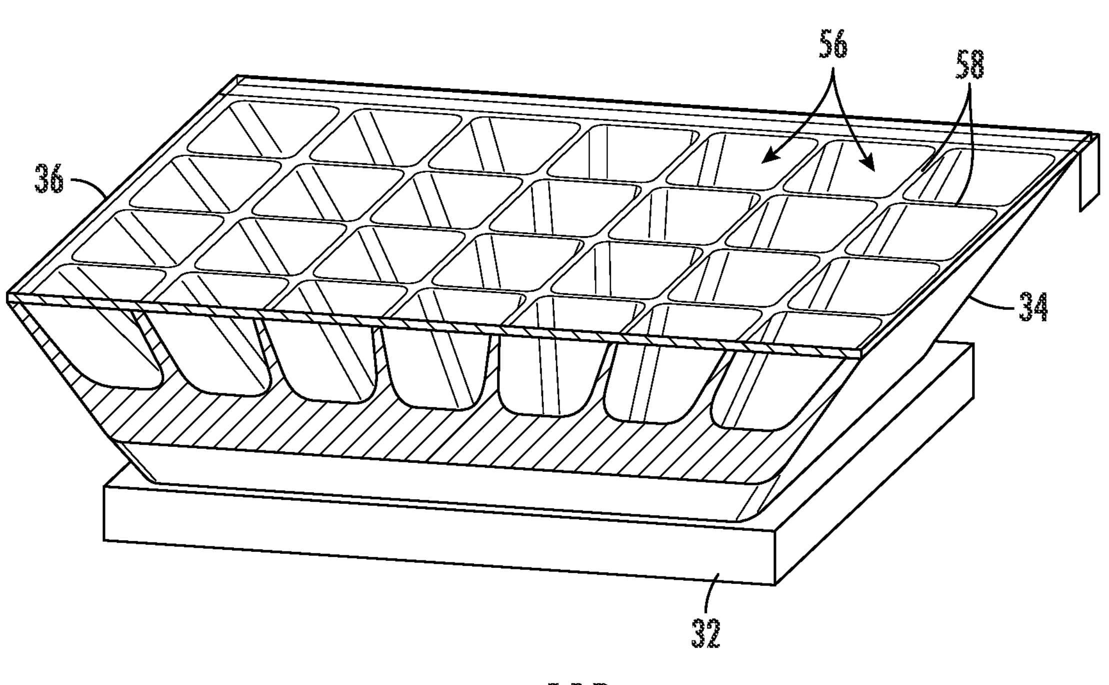
FIG. 11B is a perspective side section view of the cover of FIG. 11A in place on the funnel of FIG. 7.

Referring to FIGS. 6, 9 and 10, the funnel 34 has the general shape of a truncated inverted pyramid, with sloping side walls 54. The funnel 34 comprises multiple chutes 56 that are formed by series of dividing walls 58. The lower ends 53 of the chutes 56 are arranged so that they align with the through holes 40 in the floor 38 of the base 32. The dividing walls 58 are arranged so that the chutes 56 flare outwardly as they extend upwardly (see FIG. 10); also, the upper ends 55 of the chutes 56 are wider (in both front-to-back and side-to-side directions) than their lower ends. As a result, the upper ends 55 of the chutes 56 form a grid that is similar in arrangement to the grid formed by the lower ends 53 of the chutes 56, but with larger openings (i.e., the openings in the upper ends 55 have a greater area than the openings in the lower ends 53). In some embodiments the area of the upper ends 55 of the chutes 56 is between about 1.5 to 3 times as large as the area of the lower ends 53 of the chutes 56. Also, in some embodiments the chutes 56 have smooth walls that encourage sliding movement of medicaments therein and reduce or eliminate the production of powder or dust that might occur from the sliding of medicaments over a rougher surface.

The funnel 34 is positioned in the base 32 with its lower end captured within the rim 42 (see FIG. 6). This positioning aligns the lower ends of the chutes 56 with the through holes 40 of the base 32. The cover 36, which is generally square or rectangular (see FIG. 11A) fits over the upper end of the funnel 34 to close off all of the upper ends of the chutes 56 (see FIG. 11B—see also FIG. 6). The cover 36 is typically transparent, and may be either fixed to the funnel 34, completely detachable, or attached to permit selective access to the funnel 34 (e.g., the cover may be pivotally attached to the base 32 to allow swapping of funnels depending on the blister cards to be inspected).

Referring now to FIG. 6, the system 10 also includes a camera 80 mounted on the floor 18 of the housing 12. The camera 80 is positioned beneath the base 32 of the holder 30. The camera 80 is configured to capture images of medicaments, and is operatively connected with an inspection unit (shown schematically at 85) that is configured to receive and process the images captured by the camera 80 to determine if the proper medication has been loaded into the individual compartments of adherence packaging (e.g., the wells of a blister card, or the pouches of a pouch package). There may be a benefit to employing an inspection unit that is able to inspect the contents of both pouch packages and blister cards, as such units may include some machine learning components that may benefit from training samples from both types of adherence packaging. Additionally, in a situation where a pharmacy may package medications in both pouch and blistercard packaging, only one inspection unit may be required. An exemplary camera and inspection unit used for pouch packaging is the PARATA PERL® system, available from Parata Systems, LLC (Durham, North Carolina), which may be modified for inspecting the contents of a blister card. Other camera-based inspection systems for adherence packaging are described in, for example, U.S. Patent Publication No. 2022/0156908 to Van Schelven and PCT Publication No. 2019/170685 to Van Schelven, and U.S. Patent Publication Nos. 2022/0261982 and 2022/0254172 and 2023/0410970 to Bugay; and 2023/0098966 to Lewis, the disclosures of which are hereby incorporated herein by reference in full. In some embodiments, the system 10 may also include an illumination unit (e.g., a photographic flash or strobe) to illuminate the medicaments being inspected.

The inspection system 10 also includes a controller 95 that is operatively connected with the various components of the system 10. These include the motor 50, the camera 80, the inspection unit 85, and other components (e.g., the flash or strobe discussed above, or a drawer mechanism as discussed below, an on-off switch, etc.). The controller 95 can control the sequence of operations to ensure that they proceed smoothly. The controller 95 of the present inventive concepts may be embodied in hardware and/or in software (including firmware, resident software, micro-code, etc.). Furthermore, exemplary embodiments of the present inventive concepts may take the form of a computer program product comprising a non-transitory computer-usable or computer-readable storage medium having computer-usable or computer-readable program code embodied in the medium for use by or in connection with an instruction execution system. In the context of this document, a computer-usable or computer-readable medium may be any medium that can contain, store, communicate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, or device. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Figure 12:
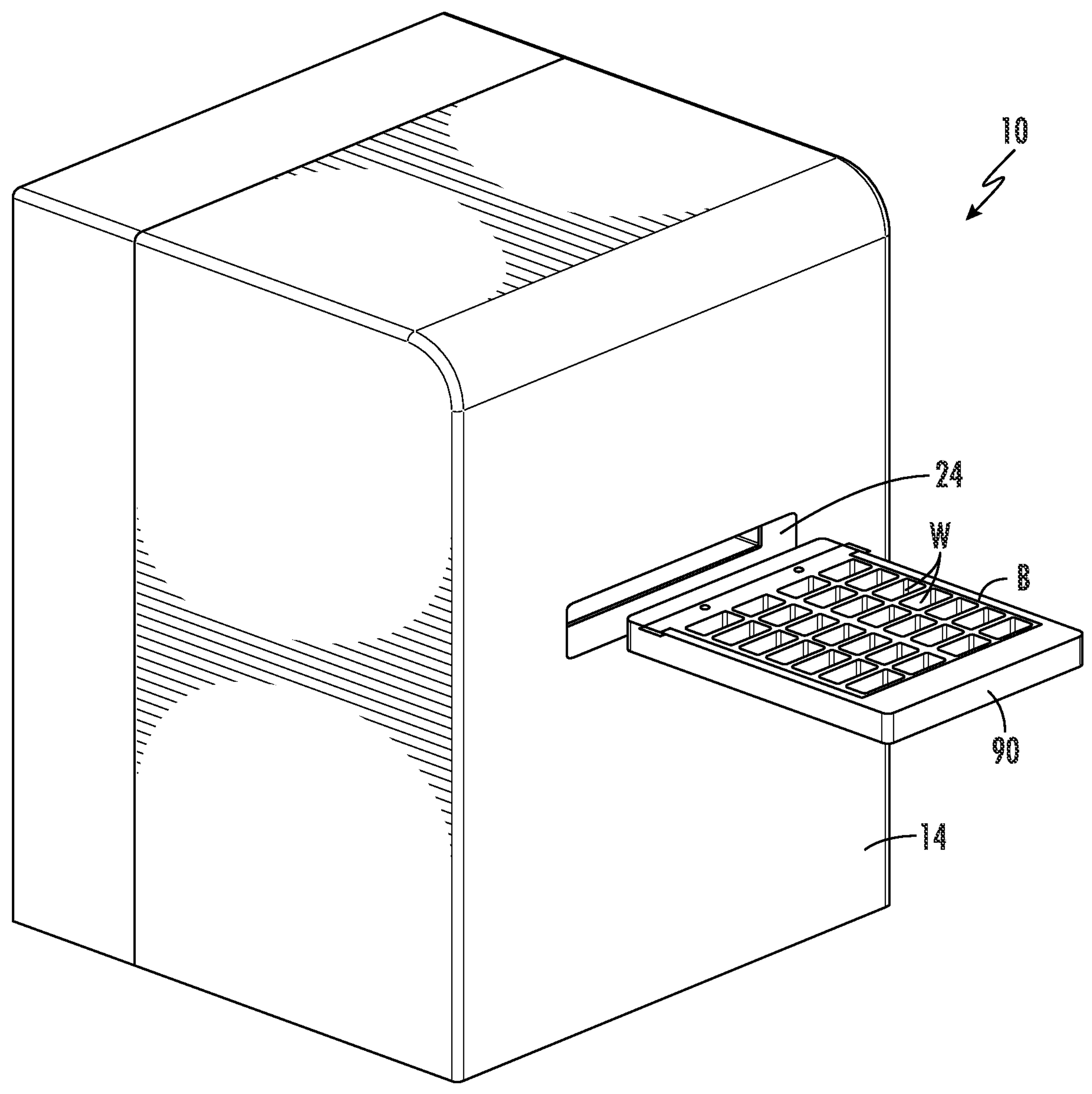
FIG. 12 is a front perspective view of the inspection system of FIG. 1 with a drawer holding a blister card loaded with medicaments being inserted into the system.
Figure 13:
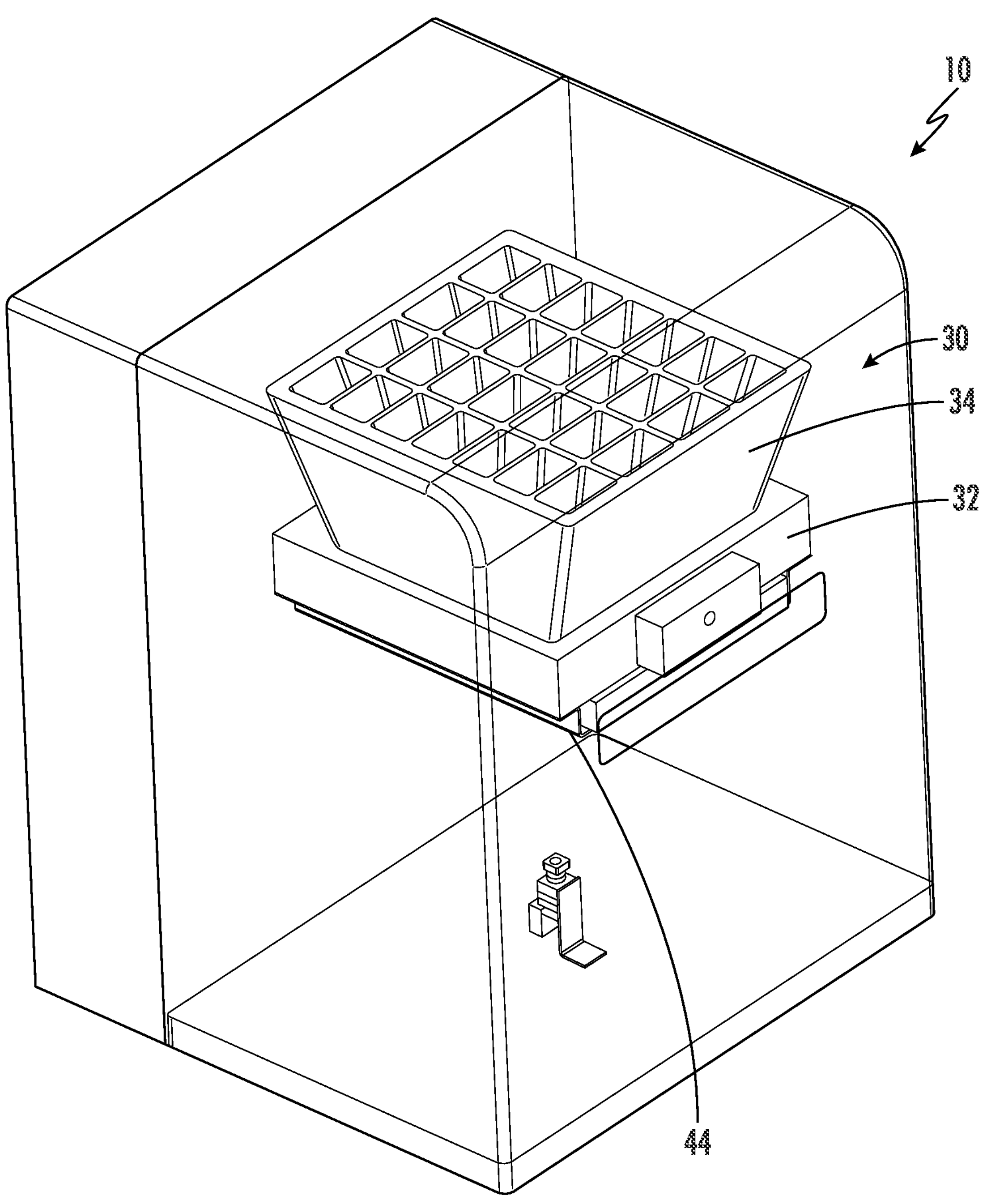
FIG. 13 is a front perspective view of the system of FIG. 1 with the blister card inserted into the pocket of the base.

Operation of the system 10 begins with the insertion of a blister card B loaded with medicaments (see FIG. 12). In some cases, the blister card B will be loaded manually, while in other cases the blister card B may be loaded automatically (e.g., with the SynMed™ XF or SynMed™ Ultra machine discussed above). In either instance, once the blister card B is loaded with medicaments, it is transferred to the system 10. Such transfer may involve covering the blister card with a plate or cover as it is transferred to assure that none of the medicaments become dislodged from their respective wells. Also, in some embodiments the blister card B may be transported in a transfer plate or tray that supports the blister card B from underneath. In some instances, the transfer plate may have a bar code, RFID tag or the like that can be read by the inspection unit 85 (either directly or via an external bar code or RFID scanner) to ensure that the system 10 knows which medicaments to expect during inspection (or in some instances the bar code, RFID tag, etc. may be located on the blister card itself). The transfer plate may also include features that help to secure the cover in place during transfer, and/or that facilitate removal of the cover to permit its use with the next blister card to be transferred As shown in FIGS. 12 and 13, once a blister card B arrives at the system 10, the blister card B may be loaded into a drawer 90. If a transfer plate is employed, in some embodiments both the blister card B and the transfer plate may be loaded into the drawer 90. Also, any cover employed during transfer from the medicament loading device is removed (removal of the cover may be done manually, or may be done automatically during insertion of the drawer 90 into the slot 24 as described below). The drawer 90 is inserted into the slot 24 in the front wall 14 of the housing 12. Such insertion leads the drawer 90 into the pocket 44 of the base 32 of the inspection holder 30. When the drawer 90 is fully inserted into the pocket 44, the wells W of the blister card B are vertically aligned with the through holes 40 in the base 32.

The drawer 90 is illustrated herein as being separable from the housing 12; however, in some embodiments the drawer 90 may be slidably attached to the housing 12 such that the drawer 90 slides out of the housing 12 through the slot 24 for receipt and removal of the blister card B and into the pocket 44 through the slot 24 for inspection. In some embodiments modifications to the drawer 90 may include springs or other securing mechanisms to maintain the drawer 90 in place during inspection as described below.

In some embodiments, the drawer 90 and blister card B may be loaded through the slot 24 manually by a user. In other embodiments, the drawer 90 and blister card B may be loaded through the slot 24 automatically (e.g., by a robotic arm or the like). As one example, the drawer 90 may be mounted on one or more slide rails mounted to the housing 12 (much like a conventional drawer in a cabinet or chest) and can be slid along such rails into the pocket 44. Other variations may also be suitable for use with the system 10.

Figure 14:
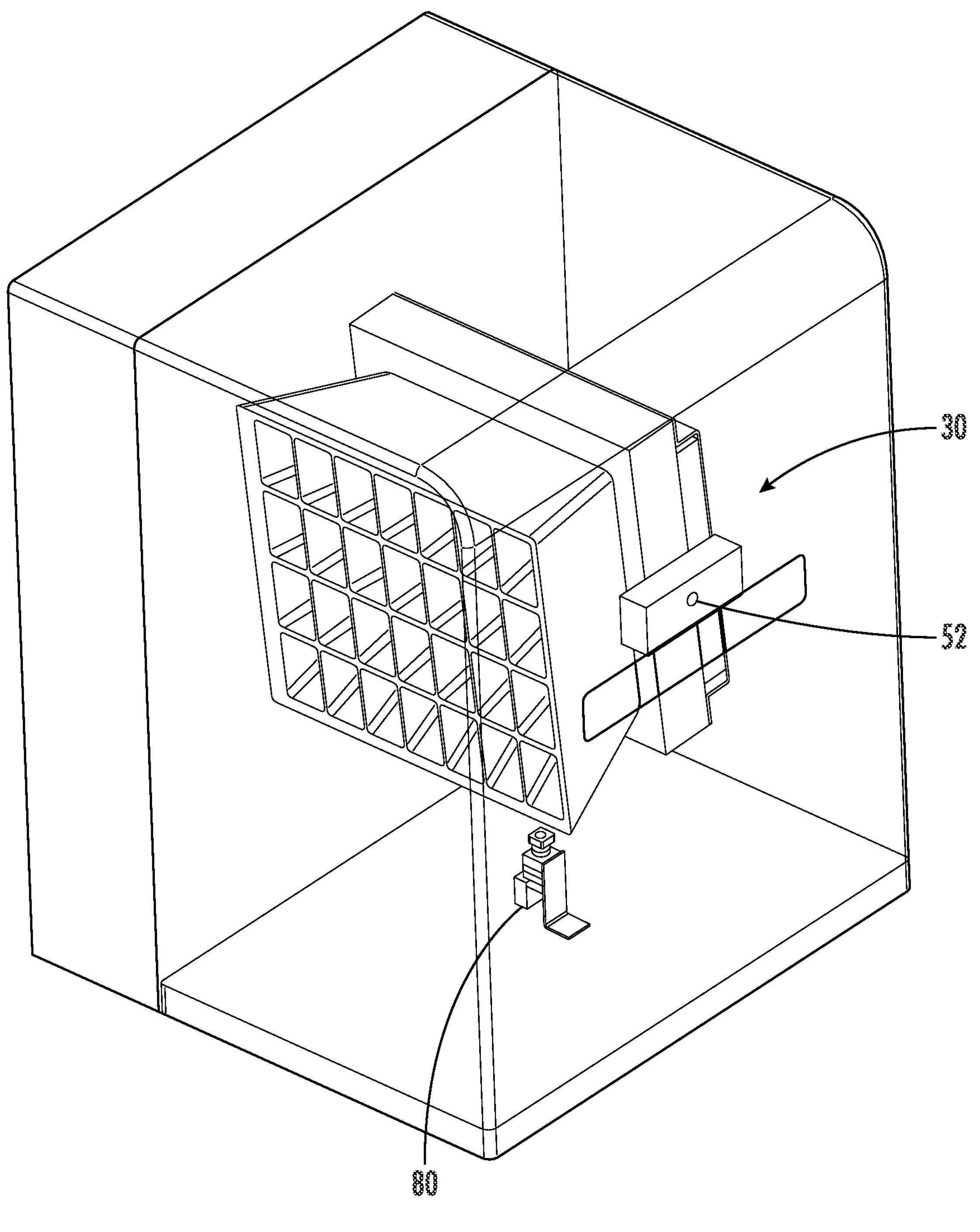
FIG. 14 is a front perspective view of the system of FIG. 1 with the inspection holder in the process of being inverted.

Once the drawer 90 is inserted into the pocket 44, the motor 50 is activated by the controller 85. This causes the inspection holder 30 (including the base 32, the funnel 34, and the cover 36) to rotate about the axis defined by the shaft 52 (see FIG. 14). As the inspection holder 30 rotates, gravity induces medicaments in the wells W of the blister card B to begin to slide from the wells W, through the through holes 40, and into the chutes 56. The inspection holder 30 continues to rotate until it is completely inverted (see FIG. 15).

Figure 15:
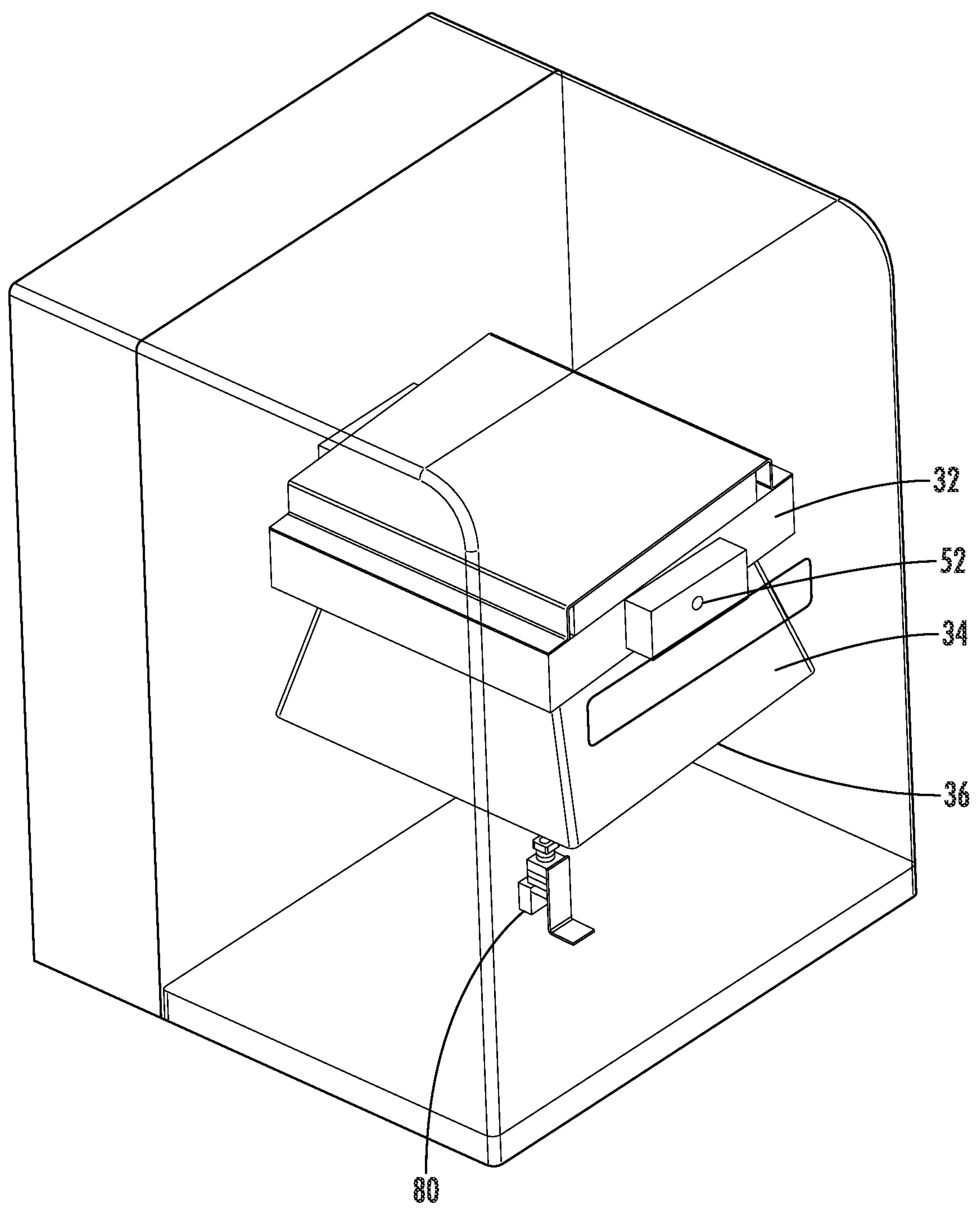
FIG. 15 is a front perspective view of the system of FIG. 1 with the inspection holder inverted so that the camera can capture images of the medicaments in the funnel as they rest on the cover.

In the inverted position of FIG. 15, the cover 36 faces the camera 80. Thus, the cover 36 acts as the lower surface of the inspection holder 30. Gravity draws the medicaments through the chutes 56 and onto the cover 36. Because the chutes 56 extend to the cover 36, the chutes 56 are closed off from each other; as a result, the medicaments of each well W remain with each other within their respective chute 56, and remain separated from the medicaments of all of the other wells W.

Once the inspection holder 30 is inverted as in FIG. 15 and the medicaments have traveled through the chutes 56 to the cover 36, the camera 80 can then be used to capture images of the medicaments. Once the images are captured, they are processed by the inspection unit 85 in a conventional manner to determine whether the medicaments (assessing number as well as identity of the medicaments based on characteristics such as their size, shape, color, markings, labeling, etc., as well as any possible defects) are correct in each well W. Because the upper ends of the chutes 56 are larger in surface area presented to the camera 80 than the wells W themselves, the medicaments tend to spread out on the cover 36 within each chute 56 over a larger area than the wells W. Consequently, the medicaments are less likely to gather in one spot, overlap, bunch together, or otherwise collect in an arrangement that is either difficult or impossible for the camera 80 to inspect.

In addition, in some embodiments, the inspection system 10 may be configured so that the inspection holder can be agitated while in the inverted position. Such agitation may be helpful if, as described above, the medicaments in one or more chutes 56 gather in an arrangement that renders precise or accurate inspection difficult. As one example, the motor 50 may quickly rotate the inspection holder 30 back and forth quickly over a small rotation angle. In other embodiments, a vibrating device may be operatively associated with the inspection holder 30 that can be selectively actuated. Other possible agitation mechanisms may be apparent to those of skill in this art. In some embodiments, the controller 95 may automatically signal for agitation before any image is captured by the camera 80. In some embodiments, the controller 95 may signal for agitation based on the initial images that are captured; if accurate identification of one or more medicaments is not possible from a capture image, the controller 95 can signal for agitation, which is then followed by capturing additional images that may provide for more accurate identification of the medicaments.

Figure 16:
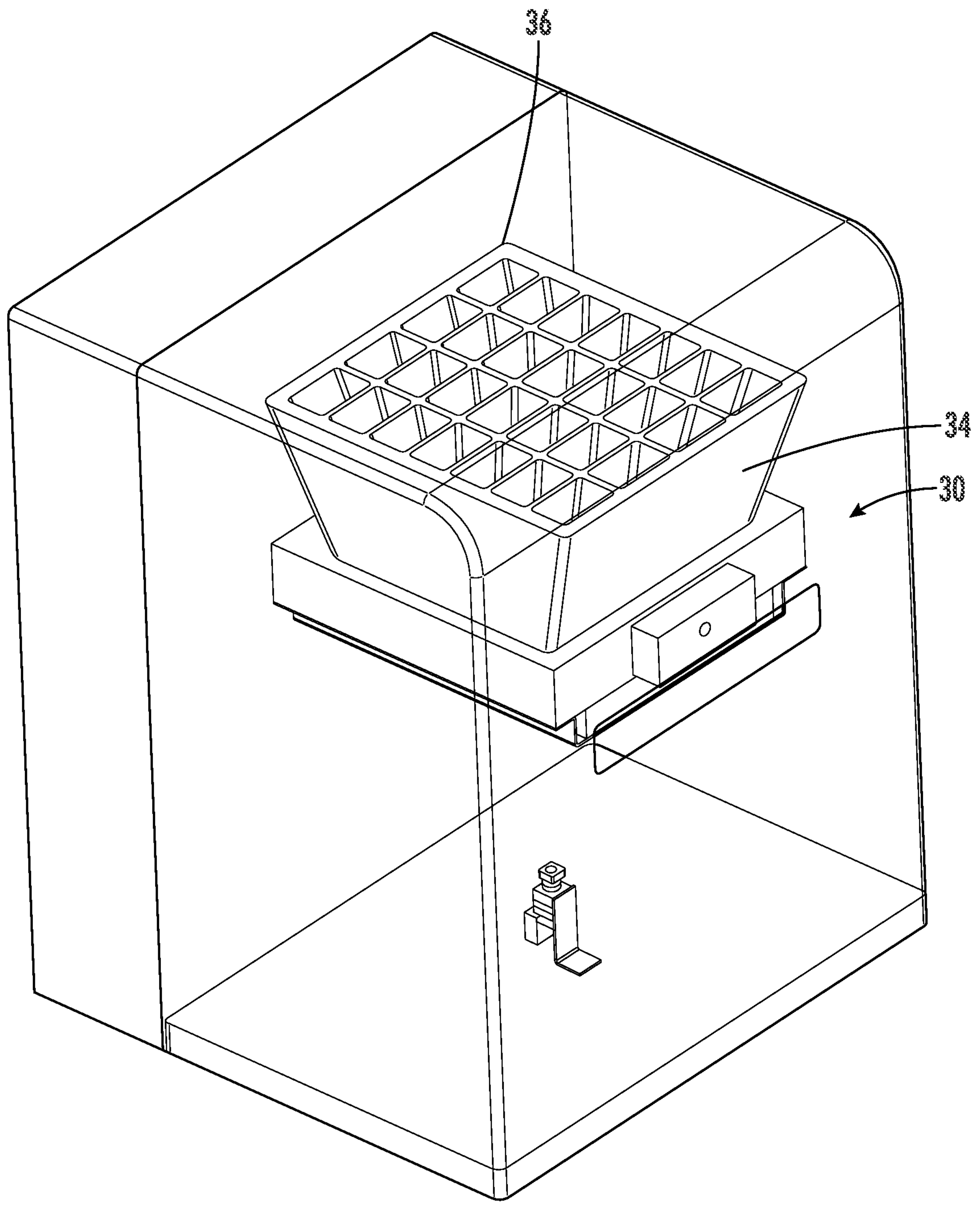
FIG. 16 is a front perspective view of the system of FIG. 1 returned to its original position after inspection by the camera.

After the camera 80 has captured the necessary images of the medicaments and forwarded the results to the inspection unit 85, the inspection holder 30 is rotated back to its original position (i.e., with the cover 36 facing upwardly—see FIG. 16). All of the medicaments slide back down their respective chutes 56 to their respective wells W of the blister card B (i.e., the wells W where they were originally loaded), as each chute 56 leads to the proper well W. As such, it is assured that each of the medicaments returns to the well W where it was originally loaded prior to inspection.

Figure 17:
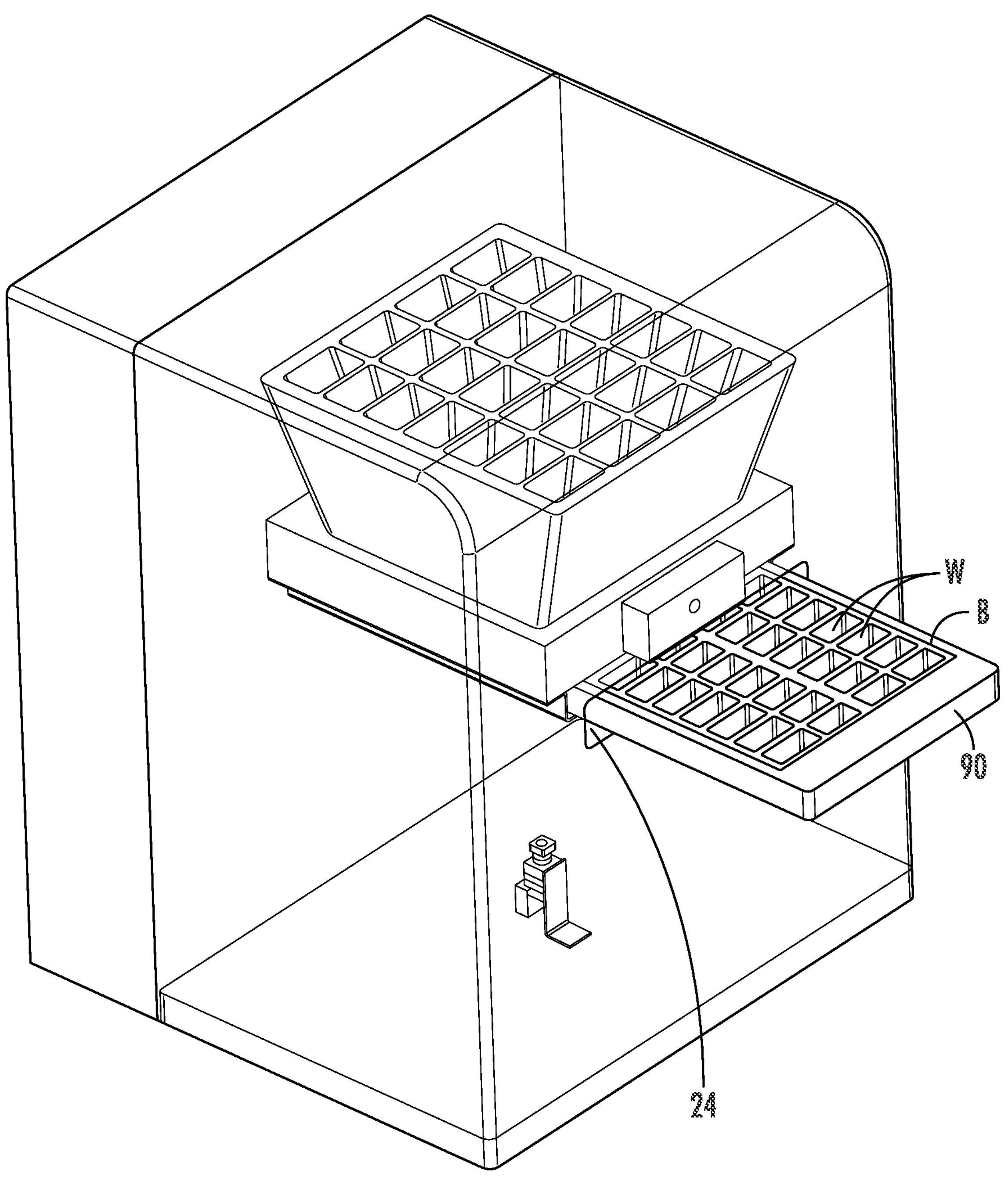
FIG. 17 is a front perspective view of the system of FIG. 1 showing the drawer and inspected blister card being removed from the system.

At this point the drawer 90 can be slid from the pocket 44 through the slot 24 so that the blister card B can be retrieved (FIG. 17). In some embodiments, a user may reach through the slot 24 to retrieve the drawer 90. In other embodiments, a robotic arm or the like may be employed to retrieve the drawer 90. In further embodiments, the inspection holder 30 may include a mechanism (e.g., a spring-loaded piston, plunger or lever) that forces the drawer 90 through the slot 24 sufficiently that it can be retrieved by a user. Other variations may also be employed.

Once removed from the housing 12, the blister card B may be sealed with a scaling sheet to capture the medicaments in their respective wells W. In some instances, the sealing sheet may include information regarding the prescription, such as the patient's identity, the identity of the medicaments, the day and time of administration for each well, the date, time and location of filling, and the like. Also, in some embodiments the system 10 may be operatively associated with a sealing device (not shown), such that the inspected blister card B is delivered automatically directly to the sealing device. The sealing device can apply a scaling sheet over the upper surface of the blister card B to seal each of the medicaments in its proper well W prior to releasing the blister card B to the user.

In some embodiments the rotational speed of the inspection holder 30 is controlled in either or both directions so that the medicaments slide within the chutes 56 within a desired speed range. In particular, the rotational speed may be selected so that the medicaments remain fully intact and do not fracture or chip as they slide from the well W of the blister card B to the cover 36 and back again.

Moreover, in some embodiments the system 10 may include a scale or other weighing system associated with the blister card B. Weighing the blister card B (either by itself or in combination with one or more other components, such as the drawer 90) before and after inspection can ensure quickly that all of the medicaments that were present in the blister card B prior to inspection are still present in the blister card B after inspection.

Further, in some embodiments a cleaning device may be included with the system 10. Such a cleaning device may be employed to clean one or both sides of the cover 36, and/or the chutes 56 of the funnel 34. In particular, the upper ends 55 of the chutes 56 may require cleaning periodically, as dust from pills may accumulate there over time. A cleaning device may include a brush to dislodge contaminants and/or a vacuum feature that removes such contaminants. As another option, the cover 36 may comprise a stretched length of plastic film that overlies the upper ends 55 of the chutes 56; the film may be stored on a roller that provides a new, clean length of film across the funnel 34 periodically.

Those of skill in this art will appreciate that, although the system 10 is illustrated as inspecting only one blister card B at a time, in other embodiments multiple blister cards B may be inspected at the same time. In such instances, a single transfer plate and/or cover such as those described above may be employed for multiple blister cards B, or multiple transfer plates and covers may be used. Such an arrangement may employ a single funnel that is configured to receive medicaments from multiple blister cards B, or may employ multiple funnels, each of which is dedicated to a single blister card B. Also, in some embodiments more than one camera 80 may be employed to capture images.

Also, those of skill in this art will appreciate that the inspection holder 30 may rotate about a different axis. For example, if multiple blister cards are inspected at once and are arranged in a single row that extends between the side walls 16 of the housing 12, the axis of rotation of the inspection holder 30 may extend between the side walls 16 to reduce the height necessary to invert the inspection holder 30.

It should also be noted that, because different arrangements of blister cards B exist, the system may employ a different funnel 34 for each different arrangement of blister card B. Alternatively, the same funnel 34 may be used for each different blister card arrangement, in which case an adapter that feeds medicaments between the blister card B and the funnel 34 may be used.

The discussion above demonstrates that the system 10 can provide a technique for inspecting medicaments loaded into a blister card without requiring a pharmacist to manually inspect the loaded blister card. This technique can save time and can improve accuracy by removing human error. The images acquired also may be stored (typically in the controller 95) as a record of the prescription filling and verification process. The images acquired by the system may be displayed on a user interface when the inspection unit 85 identifies any problems with the inspection process (i.e., particular wells where the inspection unit 85 is unable to make a positive determination that the pills contained therein are correct according to the patient's prescription, either because there is an issue with the contents of the well, such as a missing pill(s), too many pills, incorrect pill(s), damaged pill(s), etc., or the system cannot make the determination due to, for example, one or more problems with the image, unrecognized pills, or other system problem). By displaying images that have not passed the inspection, a pharmacist can view the images and make a determination as to what action needs to be taken with regard to the well(s) in question.

Alternatively, the system 10 may be used to facilitate manual inspection of the blister cards B by projecting the images acquired by the camera 80 and allowing the pharmacist to more easily view the contents of each well W so that each blistercard B does not have to be handled and the medicaments removed from the wells W for verification purposes.

Further, the system 10 may be appropriately modified to accommodate inspection of the contents of a vial or bottle of medication, so that the entire contents of the vial/bottle can be viewed by the camera 80. Modifications may include adaptation of the holder 30 and the slot 24 to accommodate a prescription vial/bottle. Additionally, the funnel 34 could be modified to a single chute 56 for a vial/bottle; there may be more than one holder 30 and funnel 34 to inspect more than one vial/bottle at a time. This would allow for verification of the correct medication and dosage for the prescription, as well ensure that all pills in the vial/bottle are identical. The inspection system 85 also may count the number of pills to ensure that the number contained in the prescription vial/bottle is correct as prescribed by the patient's physician. Such a system for inspection of vial/bottle contents may be standalone or may be incorporated into a vial/bottle filling robotic system so that vial/bottle contents are imaged and inspected prior to capping of the vial/bottle. Where the system is incorporated into a robotic vial/bottle filling system, the holder 30 may be eliminated and the robotic arm that moves the vial/bottle within the system may place the vial/bottle in association with the funnel 34 or may pour the pills from the vial/bottle into the funnel 34 which is already partially or fully inverted.

Figure 18:
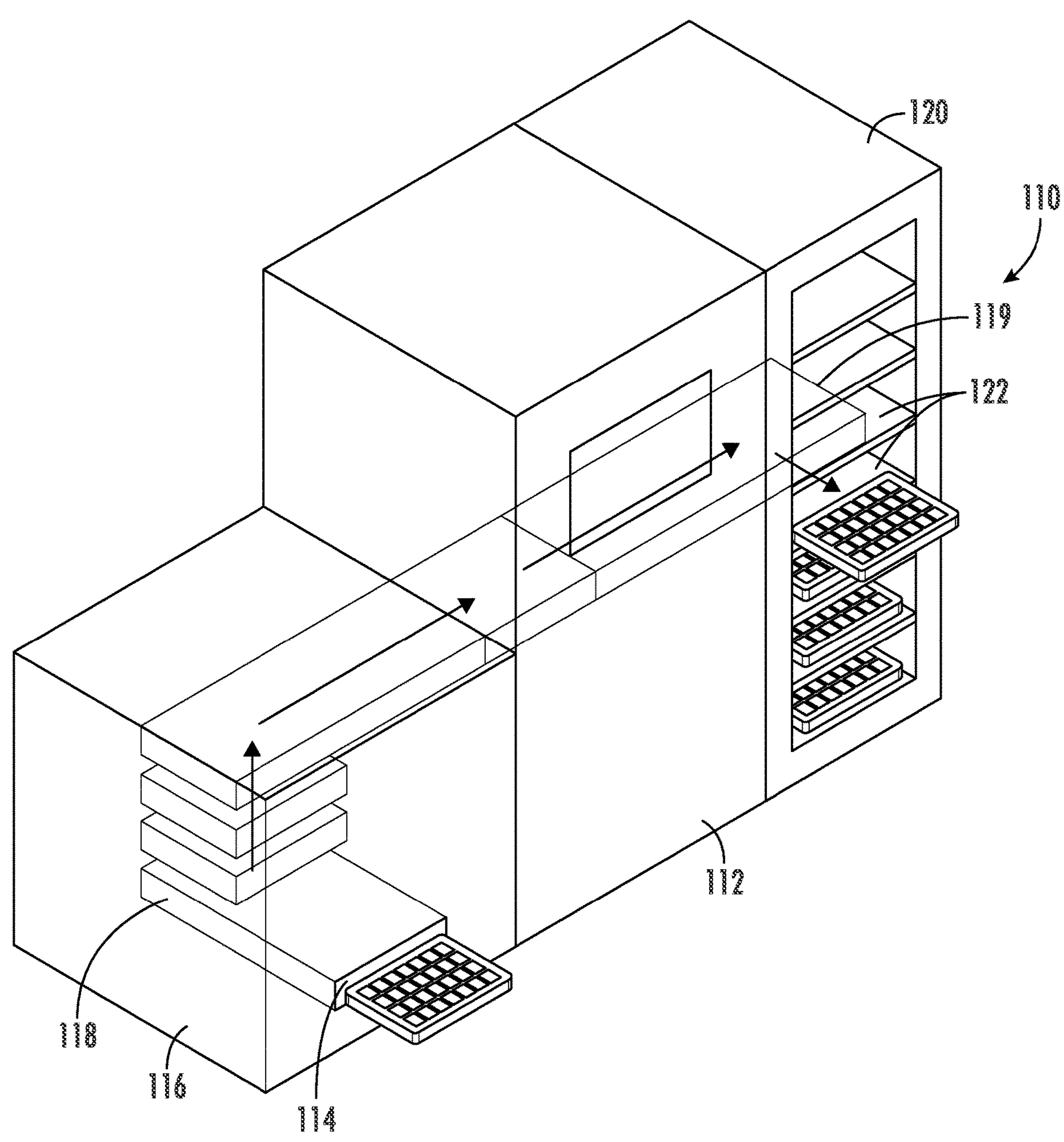
FIG. 18 is a perspective view of an inspection system according to embodiments of the invention that includes receiving and offload enclosures to facilitate throughput.

Referring now to FIG. 18, another inspection system, designated broadly at 110, is shown therein. The system 110 includes a housing 112 within which is located a blister card inspection holder and a camera (both not shown in FIG. 18) that are similar to the blister card inspection holder 30 and the camera 80 discussed above. However, the system 110 is configured such that blister cards to be inspected are inserted through a slot 114 in a receiving enclosure 116, and such that blister cards are offloaded after inspection onto one of several shelves 122 in an offload enclosure 120. A conveyor system 118 (shown schematically in FIG. 18) conveys the blister cards from the receiving enclosure 112 to the blister card inspection holder within the housing 112, and a conveyor system 119 (shown schematically in FIG. 18) conveys the blister cards from the receiving enclosure to the offload enclosure 120. Such an arrangement may facilitate throughput for the system, as offloading of a first tray, inspection of a second tray, and loading of a third tray may occur simultaneously.

The conveyors 118, 119 may be of any form suitable for conveying the blister cards without disturbing the contents of the blister cards, such as conveyor belts, chains, elevators, and the like. It should also be understood that either or both of the receiving enclosure 112 and the offload enclosure 120 may include mechanisms for loading the blister cards into the system 110 and ejecting the inspected blister cards from the system 110.

In some embodiments, the offload enclosure 120 may include a mechanism for attaching a sealing sheet to the blister card as discussed above. Moreover, the conveying mechanism 119 and/or the shelves 122 may be arranged so that, if a blister card does not pass inspection, it is delivered to a special "exceptions" shelf for processing.

Figure 19:
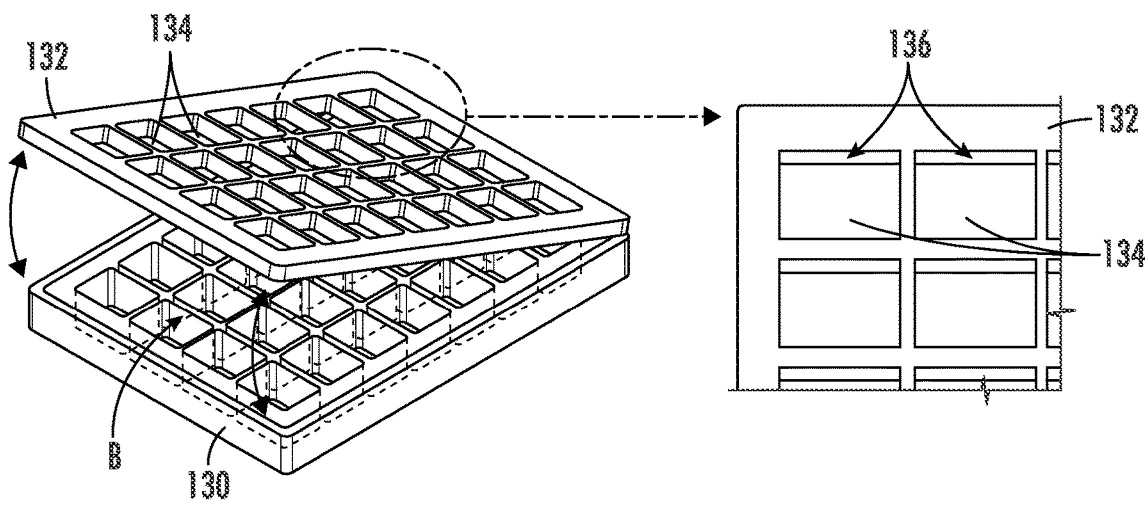
FIG. 19 is a perspective view and an enlarged partial top view of a transfer tray for blister cards that includes a cover that helps to prevent tablets from bouncing out of the wells during loading and transport.

Referring now to FIG. 19, a blister card B is shown therein occupying a transfer tray 130 that includes a protective cover 132. As shown in FIG. 19, the cover 132 may be attached to the transfer tray 130 via a hinge (not shown). The cover 132 includes holes 134, each of which has a beveled edge 136. As explained in U.S. patent application Ser. No. 18/323,247, filed May 24, 2023 (the disclosure of which is hereby incorporated herein by reference in full), the cover 132 can help to prevent tablets from "rebounding" out of the blister card during loading and/or transport.

Figure 20:
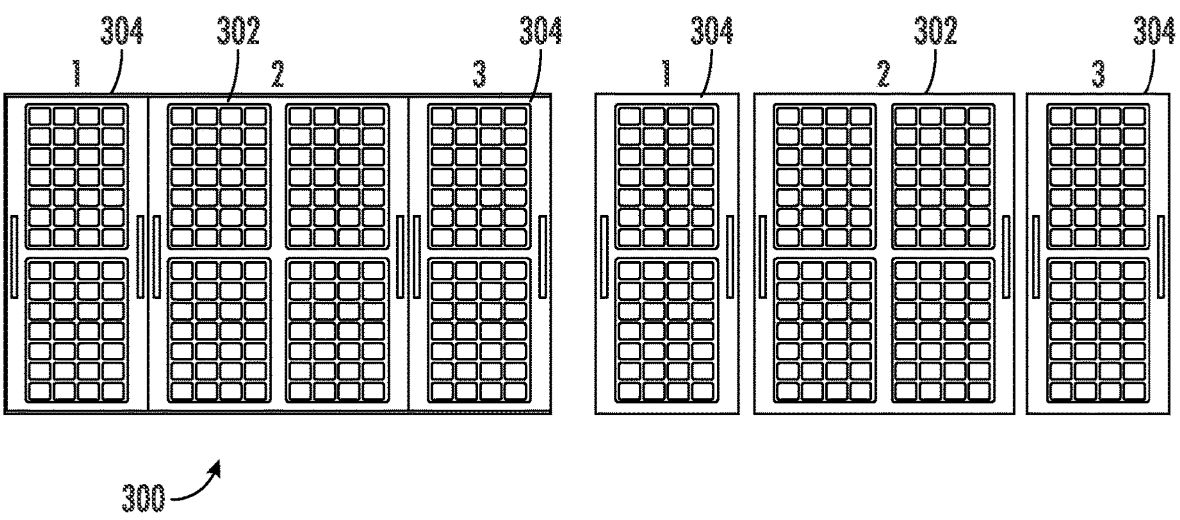
FIG. 20 is an assembled view (left side) and an exploded view (right side) of a transfer tray that may be employed with the systems of FIGS. 1 and 18.

Referring now to FIG. 20, a tray 300 is illustrated therein that can support blister cards during loading and inspection. The tray 300 includes a central main section 302 (which illustratively holds four blister cards) and two side sections 304 (which illustratively hold two blister cards each). As shown in the right-hand side of FIG. 20, the side sections 304 may be detachable from the main section 302, which may facilitate transport of the loaded blister cards to the systems 10, 110 for inspection. In addition, in some inspection systems the ability to disassemble the tray 300 may permit the tray sections themselves to be inserted into the inspection system for inspection of the loaded blister cards residing in the tray sections.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

What is claimed is:

1. A system for inspecting medicaments of a pharmaceutical prescription contained in a blister card, the blister card having a plurality of wells, each of the wells including one or more medicaments, the system comprising:

a housing;

an inspection holder rotatably mounted in the housing, the inspection holder comprising:

a funnel including a plurality of chutes with first and second ends, each of the first ends of the chutes in communication with a respective through hole, wherein each of the second ends has an area that is larger than a surface area of the corresponding first end;

a cover mounted to the funnel to cover the second ends of the chutes;

a structure for mounting a blister card filled with medicaments adjacent the first ends of the chutes;

a drive unit operatively connected with the inspection holder and configured to rotate the inspection holder between a first position, in which the cover is above the funnel, and an inverted second position, in which the cover is below the funnel;

a camera positioned below the inspection holder and configured to capture images of medicaments in the second ends of the chutes when the inspection holder is in the second position, the camera operatively connected with an inspection unit that is configured to determine whether medicaments in the captured images match medicaments expected to be in the captured images.

2. The inspection system defined in claim 1, wherein the structure for mounting a blister card comprises a base having a floor with a plurality of through holes and a receptacle for receiving the blister card filled with medicaments, each of the through holes positioned to be in communication with a respective well.

3. The inspection system defined in claim 2, wherein the housing includes a front wall having a slot, and wherein the slot is configured and positioned to enable a blister card to be inserted therethrough and into the receptacle.

4. The inspection system defined in claim 1, wherein the cover is transparent.

5. The inspection system defined in claim 1, wherein the chutes flair outwardly from first end to second end.

6. The inspection system defined in claim 1, wherein the drive unit comprises a motor and a shaft, and wherein the inspection holder is fixed to and rotates with the shaft.

7. The inspection system defined in claim 6, wherein the motor is configured to rotate the inspection holder at a rotational speed such that medicaments slide in the chutes between the first and second ends as the inspection holder is rotated between the first and second positions.

8. The inspection system defined in claim 1, wherein the system is configured to agitate the inspection holder when the inspection holder is in the second position.

9. A system for inspecting medicaments of a pharmaceutical prescription contained in a blister card, the blister card having a plurality of wells, each of the wells including one or more medicaments, the system comprising:

a housing;

an inspection holder rotatably mounted in the housing, the inspection holder comprising:

a funnel including a plurality of chutes with first and second ends, each of the first ends of the chutes in communication with a respective through hole, wherein each of the second ends has an area that is larger than a surface area of the corresponding first end;

a cover mounted to the funnel to cover the second ends of the chutes;

a structure for mounting a blister card filled with medicaments adjacent the first ends of the chutes;

a drive unit operatively connected with the inspection holder and configured to rotate the inspection holder between a first position, in which the cover is above the funnel, and an inverted second position, in which the cover is below the funnel;

a camera positioned below the inspection holder and configured to capture images of medicaments in the second ends of the chutes when the inspection holder is in the second position, the camera operatively connected with an inspection unit that is configured to determine whether medicaments in the captured images match medicaments expected to be in the captured images;

wherein the drive unit comprises a motor and a shaft, and wherein the inspection holder is fixed to and rotates with the shaft;

wherein the motor is configured to rotate the inspection holder at a rotational speed such that medicaments slide in the chutes between the first and second ends as the inspection holder is rotated between the first and second positions; and wherein the system is configured to agitate the inspection holder when the inspection holder is in the second position.

10. The inspection system defined in claim 9, wherein the structure for mounting a blister card comprises a base having a floor with a plurality of through holes and a receptacle for receiving the blister card filled with medicaments, each of the through holes positioned to be in communication with a respective well.

11. The inspection system defined in claim 10, wherein the housing includes a front wall having a slot, and wherein the slot is configured and positioned to enable a blister card to be inserted therethrough and into the receptacle.

12. The inspection system defined in claim 10, wherein the cover is transparent.

13. The inspection system defined in claim 10, wherein the chutes flair outwardly from the first end to the second end.

* * * * *